(12) United States Patent
Omoto et al.

(10) Patent No.: US 8,311,852 B2
(45) Date of Patent: Nov. 13, 2012

(54) MEDICAL INFORMATION MANAGEMENT APPARATUS

(75) Inventors: Masakazu Omoto, Orefield, PA (US); Koichi Hirose, Orefield, PA (US); Nobuaki Matsubara, Saitama (JP); Michael Ian Krupnick, Orefield, PA (US); Philip Michael Pearson, Sea Cliff, NY (US)

(73) Assignee: Olympus Medical Systems Corp., Tokyo (JP)

( * ) Notice: Subject to any disclaimer, the term of this patent is extended or adjusted under 35 U.S.C. 154(b) by 291 days.

(21) Appl. No.: 12/118,237

(22) Filed: May 9, 2008

(65) Prior Publication Data

US 2008/0281634 A1    Nov. 13, 2008

Related U.S. Application Data

(60) Provisional application No. 60/928,806, filed on May 11, 2007.

(51) Int. Cl.
*G06Q 50/00*    (2006.01)
(52) U.S. Cl. .......................................................... 705/3
(58) Field of Classification Search .................... 705/2, 3
See application file for complete search history.

(56) References Cited

U.S. PATENT DOCUMENTS

| | | | | |
|---|---|---|---|---|
| 5,072,383 A * | 12/1991 | Brimm et al. | ...................... | 705/2 |
| 7,827,041 B2 * | 11/2010 | Roberts et al. | ...................... | 705/2 |
| 8,090,593 B2 * | 1/2012 | Backhaus et al. | ................. | 705/2 |
| 2002/0082865 A1 * | 6/2002 | Bianco et al. | ...................... | 705/2 |
| 2003/0074222 A1 * | 4/2003 | Rosow et al. | ...................... | 705/2 |
| 2003/0208465 A1 * | 11/2003 | Yurko et al. | ...................... | 707/1 |
| 2007/0022086 A1 * | 1/2007 | Elsholz | ............................. | 707/1 |

FOREIGN PATENT DOCUMENTS

| | | |
|---|---|---|
| JP | 2002-073615 | 3/2002 |
| JP | 2004-118645 | 4/2004 |
| JP | 2004-348717 | 12/2004 |
| JP | 2006-146820 | 6/2006 |
| JP | 2006-260437 | 9/2006 |

OTHER PUBLICATIONS

"Statement in accordance with the Notice from the European Patent Office dated Oct. 1, 2007 concerning business methods (OJ Nov. 2007; p. 592-593)", XP002456252; ISSN: 0170-9291.
European Official Action dated May 21, 2012 from related application EP 08 008 776.0—1238.
Japanese Official Action dated Aug. 28, 2012 from related application JP 2008-123471.

* cited by examiner

*Primary Examiner* — Gerald J. O'Connor
*Assistant Examiner* — Neha Patel
(74) *Attorney, Agent, or Firm* — Scully, Scott, Murphy & Presser, P.C.

(57) ABSTRACT

A medical information management apparatus is provided which enables the person in charge of the medical services to easily keep track of the amount of services. In a medical information management apparatus according to the present invention, a task information storing unit stores the information indicating the completion of task execution or the progress of task to be executed for the task generated in a plurality of the medical services. A task number counting unit counts for each medical service the number of the tasks to be executed, and a display control unit displays for the respective medical service the number of the counted tasks on a display apparatus.

9 Claims, 17 Drawing Sheets

FIG. 4

| EXAMINATION | SCHEDULED EXAMINATION DATE | GROUP NAME | DOCTOR ID | STATUS | | | | | |
|---|---|---|---|---|---|---|---|---|---|
| | | | | EXAMINATION EXECUTION | EXAM REPORT WRITING | UNSIGNED EXAM REPORT SIGNING | PATHOLOGY REPORT WRITING | UNSIGNED PATHOLOGY REPORT SIGNING | MEDICAL FEE BILLING CODE CORRECTION |
| EXAMINATION A | MAY 1 | D | 0001 | 1 | 1 | 0 | NULL | NULL | 0 |
| EXAMINATION B | MAY 1 | D | 0001 | 1 | 1 | 1 | 1 | 1 | NULL |
| EXAMINATION C | MAY 1 | D | 0002 | 1 | 1 | 1 | 0 | NULL | NULL |
| EXAMINATION D | MAY 1 | D | 0003 | 1 | 1 | 1 | 0 | NULL | NULL |
| EXAMINATION E | MAY 1 | D | 0001 | 1 | 1 | 1 | 0 | NULL | NULL |
| EXAMINATION F | MAY 1 | D | 0002 | 1 | 1 | 1 | NULL | NULL | NULL |
| EXAMINATION G | MAY 1 | D | 0001 | 1 | 1 | 0 | NULL | NULL | NULL |
| EXAMINATION H | MAY 1 | D | 0003 | 1 | 0 | NULL | 0 | NULL | NULL |
| EXAMINATION I | MAY 1 | D | 0001 | 1 | 0 | NULL | 0 | NULL | NULL |
| EXAMINATION J | MAY 1 | D | 0002 | 1 | 1 | 1 | NULL | NULL | NULL |
| EXAMINATION K | MAY 2 | D | 0002 | 0 | 0 | NULL | NULL | NULL | NULL |
| EXAMINATION L | MAY 2 | D | 0001 | 0 | 0 | NULL | NULL | NULL | NULL |
| EXAMINATION M | MAY 2 | D | 0001 | 0 | 0 | NULL | NULL | NULL | NULL |
| EXAMINATION N | MAY 2 | D | 0002 | 0 | 0 | NULL | NULL | NULL | NULL |
| EXAMINATION O | MAY 2 | D | 0002 | 0 | 0 | NULL | NULL | NULL | NULL |
| EXAMINATION P | MAY 2 | D | 0003 | 0 | 0 | NULL | NULL | NULL | NULL |
| EXAMINATION Q | MAY 2 | D | 0001 | 0 | 0 | NULL | NULL | NULL | NULL |
| EXAMINATION R | MAY 2 | D | 0002 | 0 | 0 | NULL | NULL | NULL | NULL |
| EXAMINATION S | MAY 2 | D | 0003 | 0 | 0 | NULL | NULL | NULL | NULL |
| EXAMINATION T | MAY 2 | D | 0003 | 0 | 0 | NULL | NULL | NULL | NULL |
| EXAMINATION U | MAY 2 | D | 0002 | 0 | 0 | NULL | NULL | NULL | NULL |
| EXAMINATION V | MAY 2 | D | 0001 | 0 | 0 | NULL | NULL | NULL | NULL |
| EXAMINATION W | MAY 2 | D | 0002 | 0 | 0 | NULL | NULL | NULL | NULL |
| EXAMINATION X | MAY 2 | D | 0003 | 0 | 0 | NULL | NULL | NULL | NULL |
| EXAMINATION Y | MAY 2 | D | 0003 | 0 | 0 | NULL | NULL | NULL | NULL |
| EXAMINATION Z | MAY 2 | D | 0001 | 0 | 0 | NULL | NULL | NULL | NULL |

FIG. 5

| EXAMINATION | SCHEDULED EXAMINATION DATE | GROUP NAME | DOCTOR ID | STATUS | | | | | |
|---|---|---|---|---|---|---|---|---|---|
| | | | | EXAMINATION EXECUTION | EXAM REPORT WRITING | UNSIGNED EXAM REPORT SIGNING | PATHOLOGY REPORT WRITING | UNSIGNED PATHOLOGY REPORT SIGNING | MEDICAL FEE BILLING CODE CORRECTION |
| EXAMINATION A | MAY 1 | D | 0001 | 1 | 1 | 0 | NULL | NULL | 0 |
| EXAMINATION B | MAY 1 | D | 0001 | 1 | 1 | 1 | 1 | 1 | NULL |
| EXAMINATION E | MAY 1 | D | 0001 | 1 | 1 | 1 | 0 | NULL | NULL |
| EXAMINATION G | MAY 1 | D | 0001 | 1 | 1 | 0 | 0 | NULL | NULL |
| EXAMINATION I | MAY 1 | D | 0001 | 1 | 0 | NULL | 0 | NULL | NULL |
| EXAMINATION L | MAY 2 | D | 0001 | 0 | 0 | NULL | NULL | NULL | NULL |
| EXAMINATION M | MAY 2 | D | 0001 | 0 | 0 | NULL | NULL | NULL | NULL |
| EXAMINATION Q | MAY 2 | D | 0001 | 0 | 0 | NULL | NULL | NULL | NULL |
| EXAMINATION V | MAY 2 | D | 0001 | 0 | 0 | NULL | NULL | NULL | NULL |
| EXAMINATION Z | MAY 2 | D | 0001 | 0 | 0 | NULL | NULL | NULL | NULL |

FIG.8

TASK ASSIGNED TO DR. ABC

Date From ▭  Date To ▭

May/02/2007

⟨Task of Exam Date⟩

| Your Exams | Procedure Notes |
| (5) | (6) |

⟨Task of After Exam Date⟩

| Unsigned Exam Reports | Pathology Reports | Unsigned Pathology Reports | Non-Billable Reports |
| (2) | (3) | (0) | (1) |

FIG.14

| Colonoscopy Report | | | |
|---|---|---|---|
| Findings | | | |
| Findings | | | |
| /polyps/ | | | |
| diverticulum | | | |
| diverticulosis | | | |
| blood | | | |
| tumor | | | |
| more... | | | |

| number | size | base |
|---|---|---|
| /single/ | /small/ | /sessile/ |
| multiple | medium | flat |
| 1 | large | pedunculated |
| 2 | <5mm | semi-pedunculated |
| 3 | 5-10mm | |
| more... | >10mm | |
| appearance | bleeding | stigmata |
| firm | bleeding on contact | adherent clot |
| fungating | oozing | loose clot |
| nodular | spurting | spot |
| polypod | /not bleeding/ | visible vessel |
| smooth | | /no bleeding stigmata/ |
| view | maneuvers | |
| retroflexed view | /hot biopsy polypectomy.../ | |
| | cold biopsy polypectomy | |
| | biopsy | |
| | cytology... | | maneuvers
random biopsy
cytology
dilatation
more...

Colonoscopy Report

Findings

Findings
/polyps/
diverticulum
diverticulosis
blood
tumor
more...

maneuvers
random biopsy
cytology
dilatation
more...

402 polyps - mid sigmoid

A single small sessile polyp was found in the mid-sigmoid. It was not bleeding and showed no bleeding stigmata.

The polyp was completely removed by hot biopsy polypectomy. The polyp was retrieved and placed in jar 1.

A laser was successfully applied to ablate.

FIG.16

| Colonoscopy Report | | | | | | |
|---|---|---|---|---|---|---|
| Findings | | number | size | | base | |
| H.Pylori antibody test | | /single/ | /small/ | | /sessile/ | |
| Findings | | cytology → H.Pylori antibody test | | | flat | |
| /polyps/ | | polyps → cytology → H.Pylori antibody | | | pedunculated | |
| diverticulum | | tumor → cytology → H.Pylori antibody | | | semi-pedunculated | |
| diverticulosis | | 3 | 5-10mm | | | |
| blood | | more... | >10mm | | | |
| tumor | | appearance | bleeding | | stigmata | |
| more... | | firm | bleeding on contact | | adherent clot | |
| | | fungating | oozing | | loose clot | |
| | | nodular | spurting | | spot | |
| | | polypod | /not bleeding/ | | visible vessel | |
| | | smooth | | | /no bleeding stigmata/ | |
| maneuvers | | view | maneuvers | | | |
| random biopsy | | retroflexed view | /hot biopsy polypectomy.../ | | | |
| cytology | | | cold biopsy polypectomy | | | |
| dilatation | | | biopsy | | | |
| more... | | | cytology... | | | |

400
404
406

MEDICAL INFORMATION MANAGEMENT APPARATUS

BACKGROUND OF THE INVENTION

1. Field of the Invention

The present invention relates to medical information management apparatuses, and particularly to techniques for managing information on tasks generated in medical services

2. Description of the Related Art

Conventionally, a medical information system is suggested which displays a list of the data of scheduled injection tasks based on the orders issued on the injection procedure (e.g. patent document 1). By having such a list displayed, a person in charge of the task can confirm the schedule of the injection task; thus, the medical practice can be performed smoothly.

[Patent document 1] Japanese Laid-Open Publication No. 2004-348717

Various kinds of orders are issued in medical institutions and various kinds of tasks in accordance with the orders are generated in each case. The tasks generated are assigned to, for example, doctors and nurses. Taking endoscopic examinations as an example, the tasks, for example, examination execution and exam report writing after the examination, are assigned to the doctors, and the tasks, for example, pre-examination procedure, examination assistance, and post-examination procedure, are assigned to the nurses for the endoscopic examination orders that are issued. It may be possible for the person in charge in a small hospital to keep track of all the tasks for the day; however, it is difficult in the case of a big hospital. In addition, the progress status of the task changes. Thus, the scheduled task can be completed and a new task can be generated. Therefore, there is a strong need for the development of the technique which enables the person in charge of the medical services to easily keep track of the amount of services.

SUMMARY OF THE INVENTION

In this background, a general purpose of the present invention is to efficiently provide the information on the tasks of the medical services to the person in charge of the tasks in the medical institution.

A medical information management apparatus according to one embodiment of the present invention manages the information on a medical service, and comprises: a storing unit operative to store information indicating the completion of task execution or the progress of task to be executed for a task generated in a plurality of medical services; a task number counting unit operative to count the number of tasks to be executed for respective medical service; and a display control unit operative to display on a display apparatus the counted number of tasks for respective medical service.

Optional combinations of the aforementioned constituting elements, and implementations of the invention in the form of methods, apparatuses, computer programs, and recording mediums storing computer programs may also be practiced as additional modes of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 4 is a view showing a task table created for a group of doctors for the endoscopic examination;

FIG. 5 is a view showing a task table created for a doctor;

FIG. 8 is a view showing the number of tasks to be executed;

FIG. 14 is a view showing a word selection screen displayed on a display apparatus;

FIG. 15 is a view showing a written report;

FIG. 16 is a view showing a route for finding the desired words; and

DETAILED DESCRIPTION OF THE INVENTION

The invention will now be described by reference to the preferred embodiments. This does not intend to limit the scope of the present invention, but to exemplify the invention.

Figure 1:
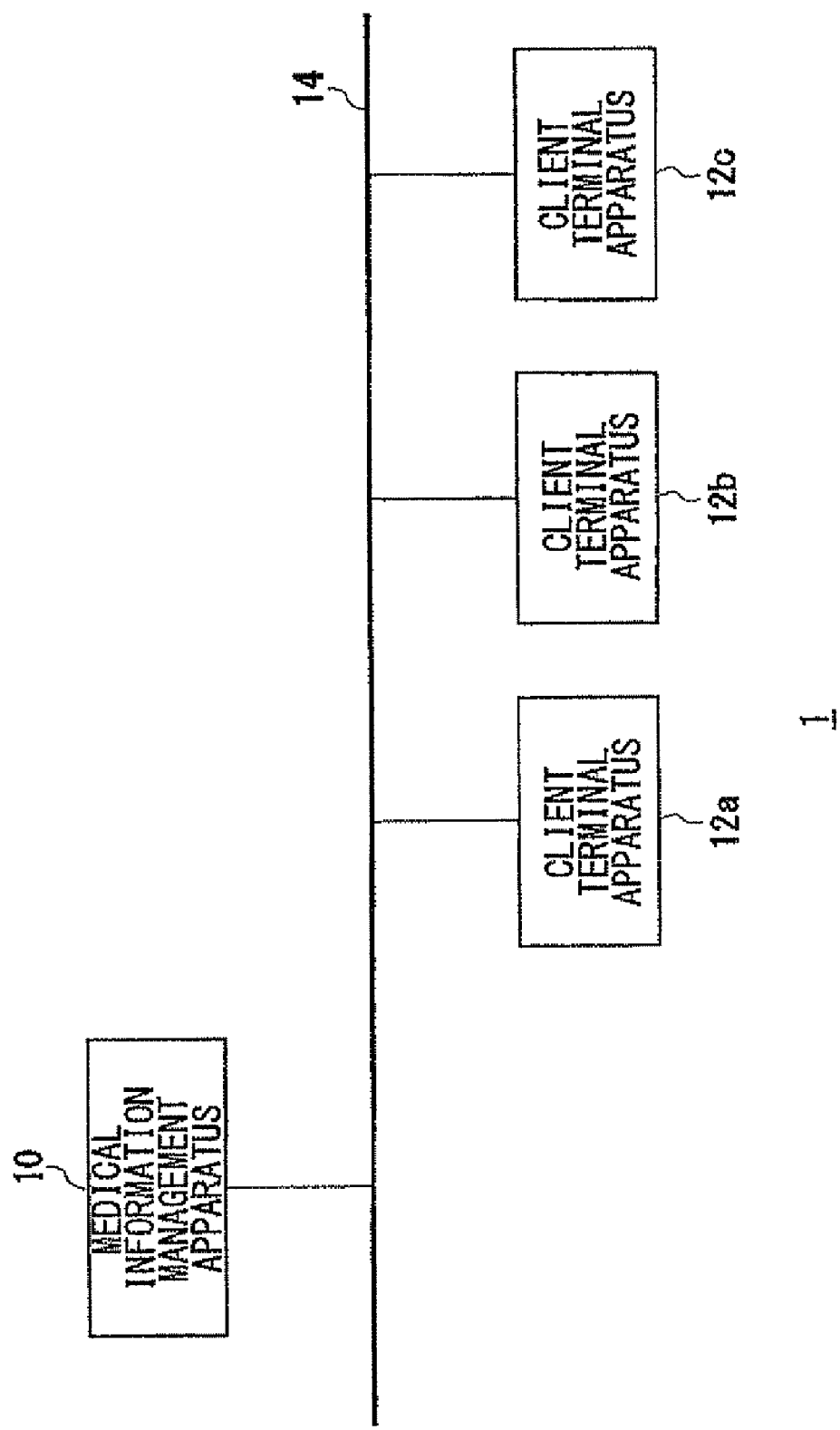
FIG. 1 is a view showing the whole configuration of a medical information management system according to the embodiment of the present invention.

FIG. 1 shows the whole configuration of a medical information management system according to the embodiment of the present invention. A medical information management system 1 is provided with a medical information management apparatus 10 and a plurality of client terminal apparatuses 12a, 12b, and 12c. The medical information management apparatus 10 and a plurality of client terminal apparatuses 12a, 12b, and 12c are connected so as to be able to communicate via a network 14. In the medical information management system 1 according to the embodiment the medical information management apparatus 10 manages the information on the medical services. More specifically, the medical information management apparatus 10 manages the task progress information indicating whether the tasks generated in a plurality of the medical services are executed or not yet executed and shows the number of tasks to be executed to the people in charge of the services, for example, doctors, nurses, receptionists, and members of the staff in the medical professions division. The medical professions division is a division in a medical institute (e.g., hospital) where medical service fees are calculated. Also, in some medical institutions, nurses sometimes serve concurrently as receptionists. The client terminal apparatus 12 is provided with an input apparatus and a display apparatus.

The client terminal apparatus 12 is used for the input of the orders on the medical practice and of the tasks generated in the medical services, and for the display of the management information from the medical information management apparatus 10. The client terminal apparatus 12 is installed in, for example, an examination room, a nurse station, and a reception space, and the input of the orders and tasks are conducted by a person in charge of the input, for example, a doctor, a nurse, and a receptionist. When an order is issued, the medical information apparatus 10 may create and register a task which is generated in relation to the order. For example, when the order for an endoscopic examination is issued, the tasks such as "pre-examination procedure", "examination execution", "examination assistance", "exam report writing", and "post-examination procedure" may be created automatically. The tasks such as "examination execution" and "exam report writing" are assigned to doctors, and tasks such as "pre-examination procedure", "examination assistance", and "post-examination procedure" are assigned to nurses.

The medical information management apparatus 10 manages the task progress information and shows the number of the tasks to be executed to respective person in charge. One type of usage of the medical information management apparatus 10 is that when a doctor reports for work, he or she places an inquiry to the medical information management apparatus 10 about the number of the tasks to be executed via the client terminal apparatus 12. The medical information management apparatus 10 returns the number of the tasks to be executed to the client terminal apparatus 12, and the doctor then confirms the number of the tasks to be executed. The number of the tasks indicates the amount of service for the day. In the case of the endoscopic examination, "examination execution" and "exam report writing" are assigned to a doctor, and the doctor can keep track of the amount of service for the day by having the number of respective tasks shown. The number of the tasks to be executed is displayed on a screen of the client terminal apparatus 12; and with this, the doctor can confirm the amounts of several types of services at a glance.

Also, during the service, the medical information management system 1 may be used for the confirmation of the number of the remaining tasks to be executed. Generally, doctors for the endoscopic examinations are charged with other kinds of services in addition to the examination execution and the exam report writing. In the endoscopic examination, the doctors for the endoscopic examination sometimes collect body tissues using endoscopes, and the collected tissues are then taken to specialists in pathology diagnosis. The diagnosis may become available on the same day, or in a few days. When the doctor for the endoscopic examination receives the pathology diagnosis, he or she has to write a report on the pathology diagnosis. This task is generated when the pathology diagnosis is received. Thus, it is possible that the task which the doctor does not see right after he or she reports for service is generated afterward. The number of the tasks to be executed decreases as the scheduled tasks get completed. Thus, the progress status of the task changes hour by hour. Therefore, by placing an inquiry about the number of the tasks to be executed to the medical information management apparatus 10 during the service, the doctor can confirm the number of the remaining tasks to be executed and check to see if new tasks are generated. By having the number of the tasks to be executed displayed on one screen, the doctor can keep track of the amount of the remaining services instantly.

Described above is the type of usage for doctors. Similarly, presenting the number of the tasks to be executed to respective person in charge who is engaged in the medical services (e.g., nurses and receptionists) permits the person in charge to keep track of the amount of remaining services instantly. For example, as for the nurses, the number of the tasks to be executed may be presented to groups instead of to individuals. This can be set at individual discretion in accordance with the service model of the medical institution, and whether the number should be presented to individuals or to groups may be determined by each medical institution.

Figure 2:
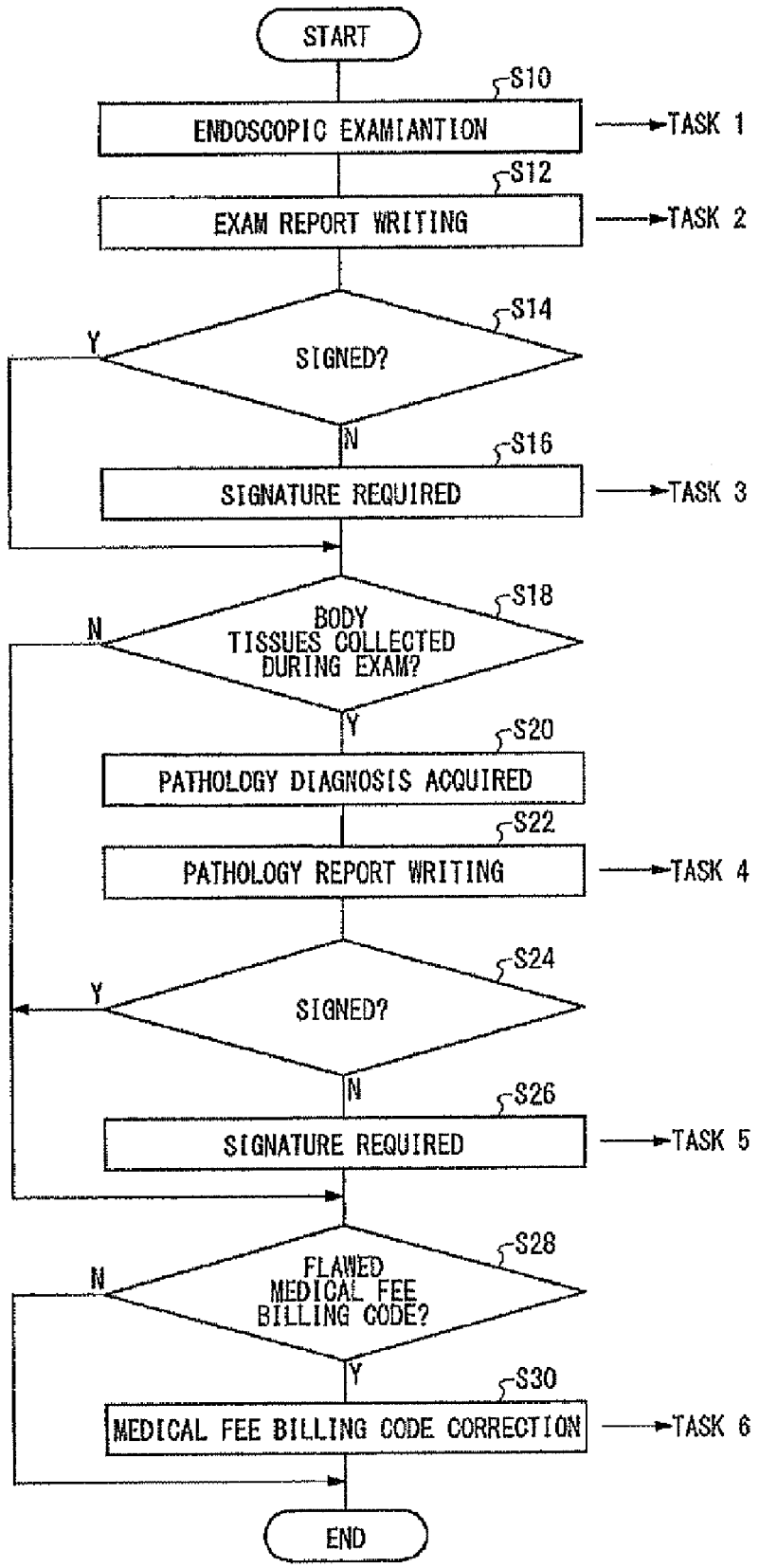
FIG. 2 is a view showing a service flow of an endoscopic examination by a doctor for the endoscopic examination.

FIG. 2 shows the service flow of the endoscopic examination by a doctor for the endoscopic examination. When the order for the endoscopic examination is issued, the doctor for the endoscopic examination performs the endoscopic examination based on the order (S10). In this case, the task "examination execution" and the task "exam report writing" after the examination are generated for the endoscopic examination order. After the completion of the endoscopic examination, exam report is written (S12) This exam report writing is done using the client terminal apparatus 12 installed in the medical office. The exam report written is sent to the medical information management apparatus 10 via a network 14. An electronic signature is required for the exam report. If there is no electronic signature in the note (N in S14), the medical information management apparatus 10 gives a notice indicating that the note is incomplete. In this case, the task "unsigned exam report signing" is generated. Upon the receipt of the notice, a doctor places an electronic signature (S16) and retransmits the note to the medical information management apparatus 10. If the electronic signature is already placed (Y in S14), the task "unsigned exam report signing" is not generated and the doctor does not need to place a signature again.

If body tissues are collected during the endoscopic examination and the collected tissues are sent to a specialist in the pathology diagnosis (Y in S18), the pathology diagnosis is sent to the doctor for the endoscopic examination on the same day or in a few days (S20). The task "pathology report writing" is generated when the pathology diagnosis is obtained and the doctor writes a pathology report (S22). The written report is sent to the medical information management apparatus 10 via the network 14. As required for the exam report, the electronic signature is required for the pathology report. If there is no electronic signature in the report (N in S24), the medical information management apparatus 10 give a notice indicating that the report is incomplete. In this case, the task "unsigned pathology report signing" is generated. The doctor places an electronic signature (S26) and retransmits the report to the medical information management apparatus 10. If the electronic signature is already placed (Y in S24), the task "unsigned pathology report signing" is not generated and the doctor does not need to place a signature again. If body tissues are not collected during the endoscopic examination (N in S18), the flow from S20 to S26 is skipped.

After the endoscopic examination, the doctor creates a medical fee billing code and transmits the code to the medical professions division. In the medical professions division, the validity of the medical fee billing code is assessed. If the code turns out not to be appropriate, the doctor is instructed to correct the code. The transmission and reception of the information are performed between the client terminal apparatuses 12. If the medical fee billing code is flawed (Y in 328), the task "medical fee billing code correction" is generated. The doctor reexamines the medical fee billing code, and retransmits the corrected code to the medical professions division (S30). If the medical fee billing code is not flawed (N in S28), the task "medical fee billing code correction" is not generated. The medical fee billing may be coded using the amount of money itself or an alternative value such as insurance points. A payment system for medical services varies in each country and should be calculated under applicable standards of the country.

The service flow of the examination by the doctor for the endoscopic examination shown in FIG. 2 is an example, and for example, the exam reports in S12 may be unified with the pathology reports in S22. In this case, after the pathology diagnosis is obtained in S20, the endoscopic examination exam reports may be written with the opinion of the pathology diagnosis. This should be performed in accordance with a system of, for example, each country or each medical institution. In any case, the task of writing an exam report is generated.

Figure 3:
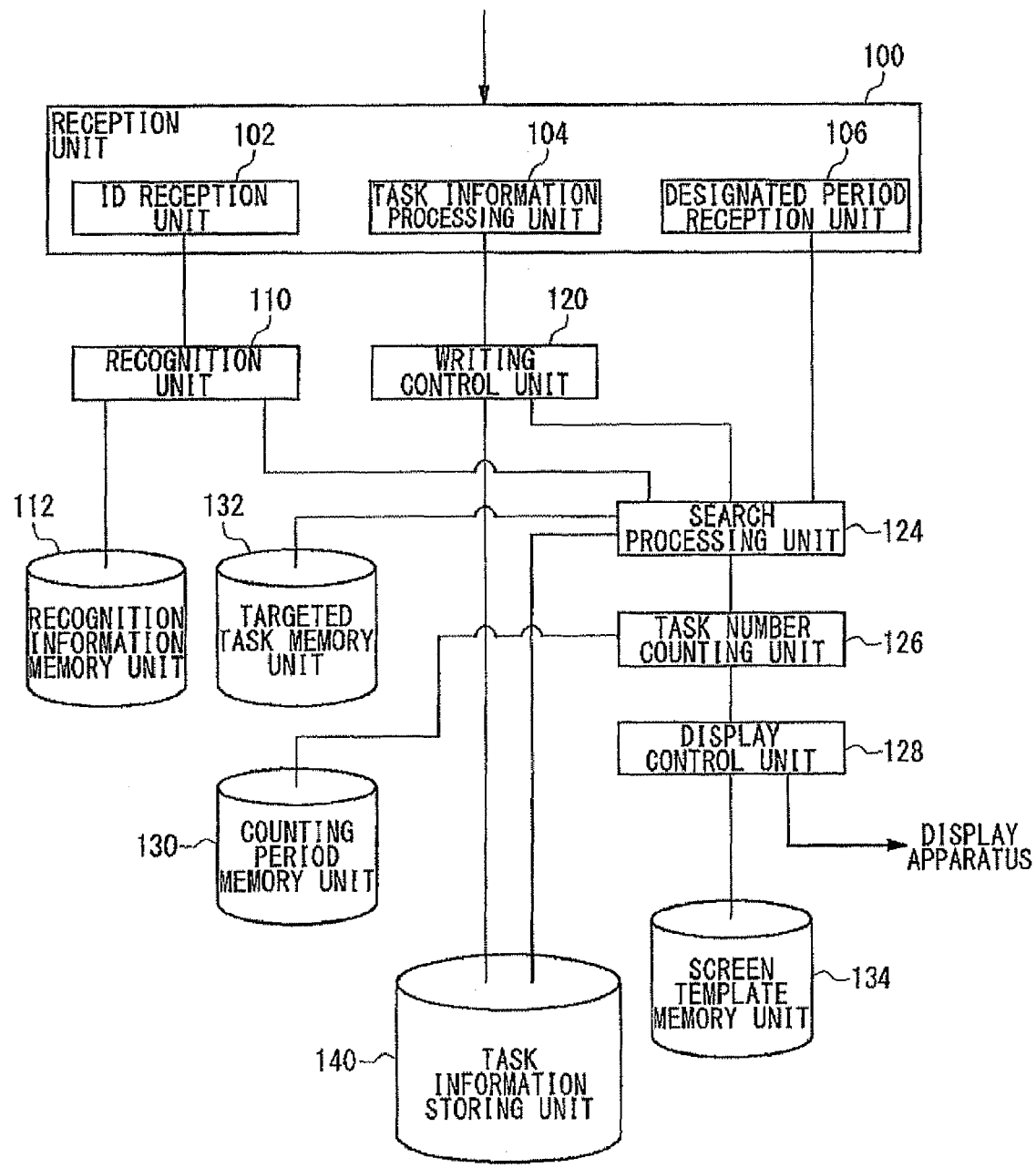
FIG. 3 is a view showing the whole configuration of a medical information management apparatus according to the embodiment.

FIG. 3 shows the configuration of the medical information management apparatus 10 according to the embodiment. The medical information management apparatus 10 is provided with a reception unit 100, a recognition unit 110, a recognition information memory unit 112, a writing control unit 120, a search processing unit 124, a task number counting unit 126, a display control unit 128, a counting period memory unit 130, a targeted service memory unit 132, a screen template memory unit 134, and a task information storing unit 140. The task information storing unit 140 stores the completion information or the progress information on the tasks generated in a plurality of medical services. The reception unit 100 is provided with an ID reception unit 102, a task information processing unit 104, and a designated period reception unit 106.

The function of the medical information management apparatus 10 may be realized by any conventional processing system or equipment, including a CPU or memory of any computer, a memory-loaded program, or the like. Here, the drawing shows a functional block configuration which is realized by cooperation between the hardware components and software components. It should be understood by a person skilled in the art that these functional blocks can be realized in a variety of forms by hardware only, software only or the combination thereof.

The task information processing unit 104 accepts the information on the tasks (task information). The task information may be transmitted from the client terminal apparatus 12 connected to the network 14, or input through an input apparatus of the medical information management apparatus 10. One of the task information is "generated task information" including the information that identifies the generated task and the information associated with the task. Upon the receipt of the issued order, the task information processing unit 104 may develop the order into a plurality of tasks and create a plurality of generated task information items. In this case, the task information processing unit 104 generates the generated task information based on the issued order. The task information processing unit 104 has a function of generating information on first tasks that are necessarily generated for the issued order and information on second tasks that are generated in accordance with the situation. The information on the second tasks is generated in accordance with the result of performing the first tasks. The task identifying information may comprise a type of the medical services and a task ID. Moreover, the associated information may include the identification information on the person or group in charge of executing the generated task, and a scheduled execution date (time). For example, the generated task information is constituted as shown in the following.

Medical Service: Endoscopic Examination
Task ID: 0001
Scheduled Execution Date: May 1
Person in Charge: Dr. A
The services, for example, the endoscopic examination and the exam report writing, are set to include the scheduled execution dates. On the other hand, the services generated after the examination, for example, the pathology report writing, may not necessarily include the scheduled examination dates.

Another task information is the task progress information indicating the progress of the task. The initial status of the generated task is "unexecuted" and when the execution of the task is completed, the task progress information indicating "execution completed" is transmitted to the medical information management apparatus 10. Thus, the task progress information may be constituted as shown in the following.

Medical Service: Endoscopic Examination
Task ID: 0001
Status: Execution Completed
The status "unexecuted" may be included in the generated task information; however, since the task just generated is always "unexecuted", the task information processing unit 104 may specify that the status is unexecuted by generating the generated task information based on the order or by accepting the generated task information from the client terminal apparatus 12.

Upon the receipt of the task information, the task information processing unit 104 processes so that the writing control unit 120 writes the task information into the task information storing unit 140. The task information storing unit 140 stores the task information in a database. For example, the task information may be stored in a relational database having storage tables of the respective medical services related to one another. With this, the task information storing unit 140 can store a task identified by the medical service and the task ID in relation with the scheduled execution date, the identification information on the person or group in charge, and the status. As described above, since the task information storing unit 140 stores the task information, the medical information management apparatus 10 can present the progress status of the task to the user.

The ID reception unit 102 receives an ID and a password from a user. The recognition information memory unit 112 stores IDs and passwords of the users or the groups belonging to a medical institution, and the recognition unit 110 authenticates the validity of the IDs and the passwords received by the ID reception unit 102 by referring to the IDs and the passwords stored in the recognition information memory unit 112. Upon the appropriate authentication of the ID and the password input, the recognition unit 110 instructs the search processing unit 124 to find the task information on the user or on the group to which the user belongs.

The targeted service memory unit 132 stores medical services for which the number of tasks to be executed is counted, for respective person or group in charge. For example, the targeted service memory unit 132 stores, in relation to the doctor for the endoscopic examination, the medical services (e.g., endoscopic examination and exam report writing) as the services subject to search Also, the targeted service memory unit 132 stores, in relation to the nurse for the endoscopic examination, the medical services (e.g., pre-examination procedure, examination assistance, and post-examination procedure) as the services subject to search. For example, in a small-scale medical institution, nurses for the endoscopic examination may take charge in reception services at the medical institution; in that case, the targeted service memory unit 132 may store, in relation to the nurse, the medical services in relation with the reception service to be searched. As described above, the correspondence of the person or group in charge with the medical services that are subject to search may be set as appropriate for every medical institution.

The search processing unit 124 searches for the task of the medical services related to the user ID authenticated by the recognition unit 110 by referring to the task information stored in the task information storing unit 140. More specifically, the search processing unit 124 extracts from the task information storing unit 140 the task linked to the person or group in charge identified by the user ID, and creates a task table for the medical services stored in the targeted service memory unit 132.

FIG. 4 shows a task table created for a group of doctors (the group is referred to as D) for the endoscopic examination comprising three doctors whose doctor IDs are 0001, 0002, and 0003, respectively. In the task table, the tasks "examination execution", "exam report writing", "unsigned exam report signing", "pathology report writing", "unsigned pathology report signing", and "medical fee billing code correction" become associated with the progress information thereof. In the example shown in FIG. 4, the task table is created for the examinations scheduled on May 2 or May 1 for the purpose of explanation; however, in reality, the tasks generated for the examinations prior to May 1 (i.e., examinations performed on April 30 or prior) are also subject to search.

In FIG. 4, "examination execution", "exam report writing", "unsigned exam report signing", "pathology report writing", "unsigned pathology report signing", and "medical fee billing code correction" indicate the tasks for the medical services of which the doctors for the endoscopic examination are in charge. For each medical service, tasks are generated having "endoscopic examination order" as a unit. Referring to FIG. 2, the tasks "examination execution" and "exam report writing" are required for the endoscopic examination and other tasks are generated in accordance with the situation, for example, during the examination.

In FIG. 4, the record "1" indicates that the task is executed and the record "0" indicates that the task is to be executed. Also, the record "NULL" indicates that the task is not generated.

For example, taking an examination A assigned to the doctor identified by ID0001 as an example, the tasks generated for each service "examination execution" and "exam report writing" are executed. On the other hand, the tasks generated for the tasks "unsigned exam report signing" and "medical fee billing code correction" are unexecuted. Also, no task is generated for the services "pathology report writing" and "unsigned pathology report signing". This indicates that the examination A is progressing as described in the following.

First, the doctor completed the endoscopic examination and the exam report writing. However, since the doctor did not sign the examination report, he or she needs to resubmit the examination report. Also, since the doctor did not collect any biopsy materials followed by pathology diagnosis, the tasks associated with the pathology diagnosis are not generated. Moreover, there is an error in coding the medical fee billing and the doctor is reminded by the medical professions division to correct the code. The above described situation is shown in the task table as the progress information. As will hereinafter be described in detail, the number of the tasks to be executed is calculated and shown to the person in charge.

FIG. 5 shows a task table created for a doctor whose doctor ID is 0001. In general, a doctor often attends to patients by himself or herself. Thus, as for doctors, the task table is preferably created individually for every doctor. In contrast, since nurses often work in a group, the task table not for the individual nurses but for the group can be preferably created. Since the situation varies from one medical institution to another, whether the task table is created for the individuals or for the group is preferably set accordingly for every medical institution.

In FIGS. 4 and 5, the date shown as the scheduled examination date is the date when the tasks for "examination execution" and "exam report writing" are executed. More specifically, as for the examination A, the endoscopic examination and the exam report writing are scheduled on May 1, and as for the examination L, they are scheduled on May 2. In the exemplary embodiment, there is no schedule set for other tasks; however, if there are tasks to be completed urgently, a schedule may be set for those tasks.

The counting period memory unit 130 stores the period for which the number of the tasks to be executed is counted. In the exemplary embodiment, the counting period memory unit 130 is set so that the number of the tasks to be executed on the day is counted in order for the doctors and nurses to be able to confirm the number of the tasks to be executed on the day. Thus, the counting period memory unit 130 stores the period as "today" for which the number of the tasks to be executed is counted. For example, the counting period for the medical professions division which is responsible for counting the medical service fees may be stored as "today and in the past". As stated above, the targeted service memory unit 130 stores the period for counting the number of the tasks to be executed in accordance with the service content of the person or group in charge.

The counting period may be changed by the designation from the user. Having received the designation of the counting period from the user, the designated period reception unit 106 may give a notice of the designated period to the task number counting unit 126. Even though the counting period memory unit 130 stores the counting period set by default, if the counting period is separately designated by the user, the task number counting unit 126 can apply the designated counting period as a set value. For example, when he or she wishes to check the number of the tasks to be executed on the following day or later, the doctor only needs to designate the counting period through the input apparatus.

The task number counting unit 126 counts the number of the tasks to be executed for each medical service based on the task table created. Using an example of the doctor for endoscopic examination identified by doctor ID 0001, the task number counting unit 126 counts the number of the tasks to be executed for each medical service as shown in the following, by referring to FIG. 5. In FIG. 5, the tasks to be executed are expressed by "0", and the number of "0's" is counted for the respective medical service.

(examination execution) 5 cases
(exam report writing) 6 cases
(unsigned exam report signing) 2 cases
(pathology report writing) 3 cases
(unsigned pathology report signing) 0 case
(medical fee billing code correction) 1 case The display control unit 128 reads out a screen template for display from the screen template memory unit 134 based on the user ID received at the ID reception unit 102. The screen template is a display form prepared for the respective person or group in charge, and characters and pictures showing the medical service of which the person or group is in charge are preferably displayed. Thus, different screen templates are prepared for doctors and nurses, and different screen templates are prepared for the doctors of respective specialties.

Figure 6:
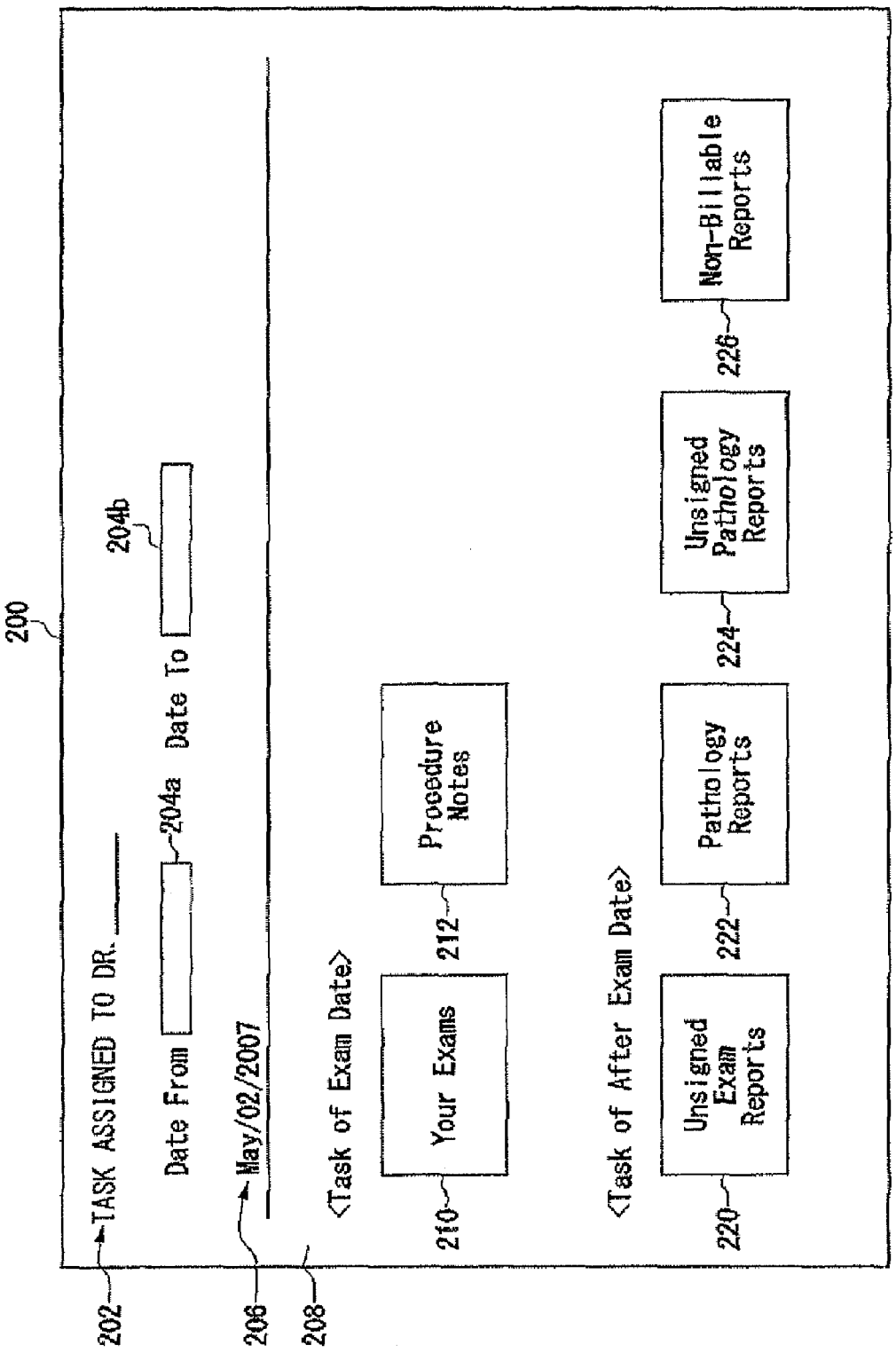
FIG. 6 is a view showing a screen template prepared for a doctor.

FIG. 6 shows a screen template 200 prepared for a doctor. A doctor display column 202 showing a user ID is provided in the screen template 200. Date input columns 204*a* and 204*b* are provided so that the user can designate the counting period of the tasks to be executed, and when the user inputs the date in the data input column 204, the information on the designated period is received at the designated period reception unit 106. The date of the day is displayed in a counting date display column 206.

Icons 210, 212, 220, 222, 224, and 226 showing the details of medical services are provided in a unexecuted task display column 208, and the number of the tasks to be execute which is counted by the task number counting unit 126 is displayed in association with each icon. The icon 210 indicates the examination service, and the icon 212 indicates the exam report writing service. The examination service and the exam report writing service are the services to be performed on the day, and in this example, the services are scheduled to be performed on May 2, 2007.

The icon 220 indicated the unsigned exam report signing service. The icon 222 indicates the pathology report writing service, and the icon 224 indicates the unsigned pathology report signing service. Moreover, the icon 226 indicates the medical fee billing code correction service.

Figure 7:
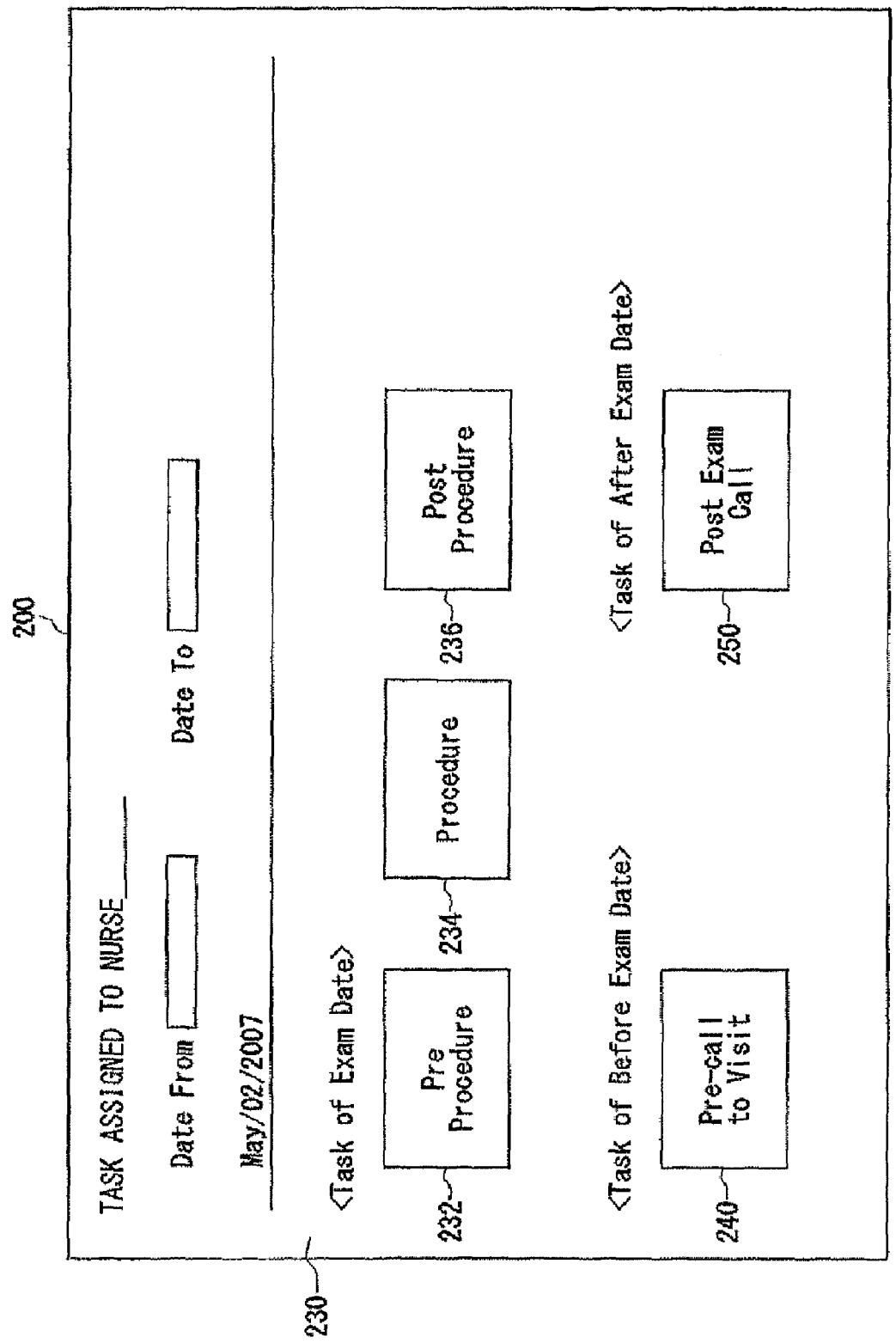
FIG. 7 is a view showing a screen template prepared for a nurse.

FIG. 7 shows the screen template 200 prepared for nurses. Icons 232, 234, 236, 240, and 250 indicating the details of medical services are provided in a unexecuted task display column 230, and the number of the tasks to be executed which is counted by the task number counting unit 126 is displayed in association with each icon. The icon 232 indicates the pre-procedure service for the examination, the icon 234 indicates the examination assisting service during the examination, and the icon 236 indicates the post-procedure service after the examination. These are the services to be performed on the day, and in this example, the services are scheduled to be performed on May 2, 2007.

The icon 240 indicates pre-call to visit service, or the service to call a patient before the scheduled examination date set on May 2 or later. The icon 250 indicates post exam call service, or the service to call the patient who has already completed the examination in order to check the condition after the examination.

FIG. 8 shows the number of the tasks to be executed being displayed for Dr. ABC. The identification number of Dr. ABC is "0001". The display control unit 128 obtains the screen template for doctors (see FIG. 6) from the screen template memory unit 134, embeds in the screen template the number of the tasks to be executed which is counted by the task number counting unit 126, and creates a display screen. The display screen is preferably built in the size so that the whole screen is displayed on the display S apparatus and that the number of the tasks is displayed for respective medical services. Dr. ABC can confirm the number of the tasks to be executed by him or her on the display apparatus installed in the client terminal apparatus 12. For example, the user may check the number of the tasks to be executed right after he or she reports for work or during the service. Preferably, the latest remaining status of the tasks is displayed on the display apparatus, and the user can easily keep track of the amount of remaining service by catching the numbers of tasks to be executed in one screen.

Figure 9:
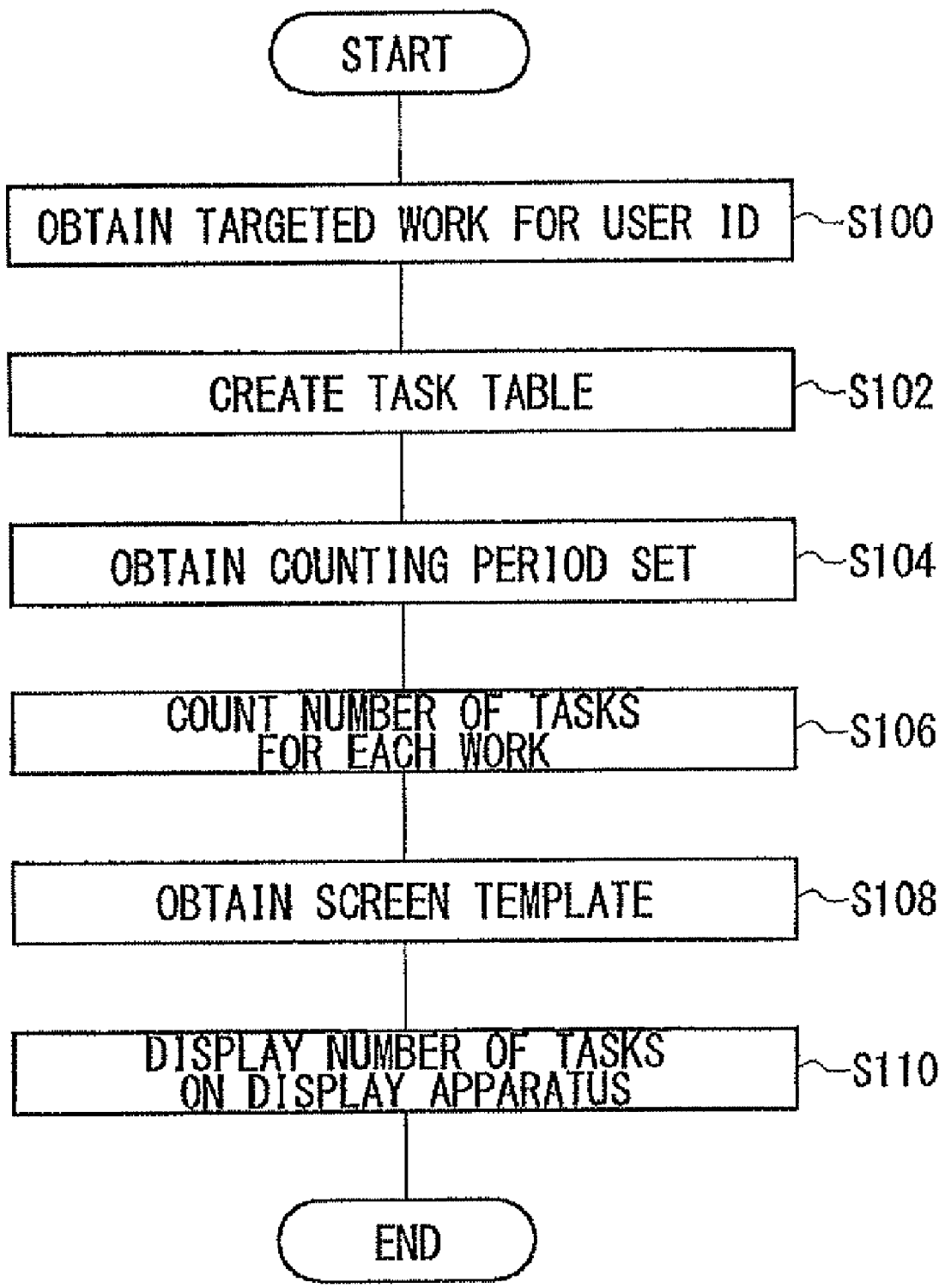
FIG. 9 is a view showing a flow to display the number of tasks to be executed.

FIG. 9 shows the flow to display the number of tasks to be executed. When the ID reception unit 102 receives an ID and a password form a user, the input ID and password are authenticated by the recognition unit 110. Upon the indication of successful authentication by the recognition unit 110, the search processing unit 124 obtains from the targeted task memory unit 132 the service set to be targeted by the user ID (S100). The search processing unit 124 obtains the status of the task progress for the targeted service which is linked to the user ID from the task information storing unit 140 and creates a task table (S102).

The task number counting unit 126 obtains the counting period set from the counting period memory unit 130 (S104). When the counting period designated by the user is received at the designated period reception unit 106, the task number counting unit 126 obtains the counting period. The task number counting unit 126 counts the number of the tasks to be executed in accordance with the set counting period (S106). The display control unit 128 obtains the screen template which corresponds to the user ID (S108), embeds the number of the tasks to be executed in the screen template, and displays the screen template on the display apparatus (S110).

Figure 10:
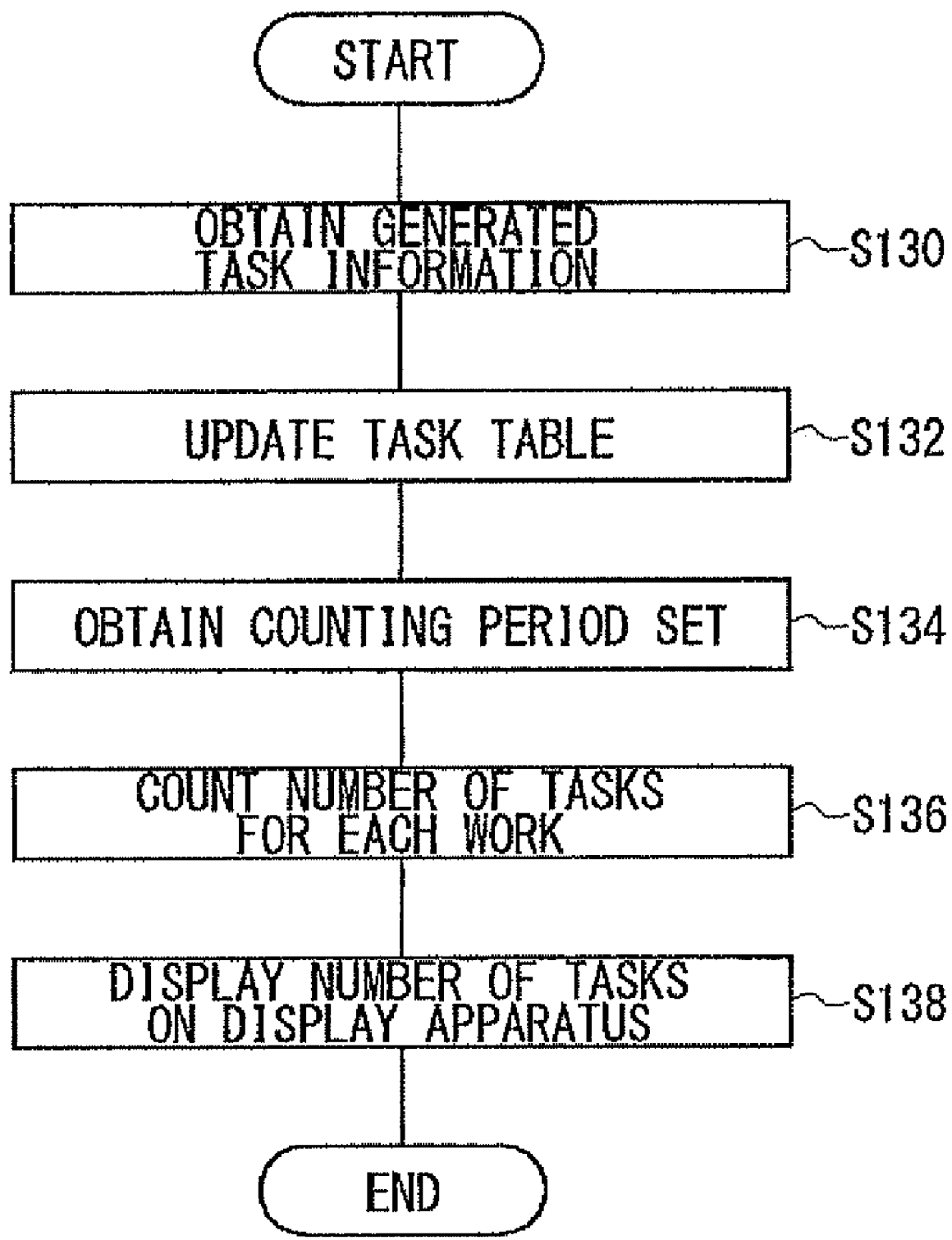
FIG. 10 is a view showing a display updating flow when a task is generated during the display of the number of tasks to be executed.

FIG. 10 shows the display updating flow when a task is generated during the display of the number of the tasks to be executed. When the task information processing unit 104 generates or receives the generated task information (S130), the writing control unit 120 writes the generated task information in the task information storing unit 140. In S130, when an order is inputted from the client terminal apparatus 12, the task information processing unit 104, after receiving the issued order, may generate task information for the tasks necessarily generated for the order. The task information processing unit 104 has a table storing the order in association with the tasks necessarily generated for the order and generates the generated task information using the table. For example, when receiving an order for an endoscopic examination, the task information processing unit 104 generates the generated task information for the "examination execution" and the "exam report writing". The status for the tasks included in the generated task information is set to "unexecuted". The search processing unit 124 updates the task table, taking into account the generated task information written in the task information storing unit (S132). The task number counting unit 126 obtains the counting period set from the counting period memory unit 130 (S134) and counts the number of the tasks to be executed in accordance with the set counting period (S136). The display control unit 128 embeds the number of the tasks to be executed in the screen template and displays the screen template on the display apparatus (S138).

In S130, the task information processing unit 104 may generate information on new tasks in accordance with the result of performing the tasks. Referring to FIG. 2, the task information processing unit 104 determines whether the electronic signature is placed upon the receipt of the written report (S14 in FIG. 2). When it is determined that there is no electronic signature (N in S14 in FIG. 2), the task information processing unit 104 generates the generated task information for "unsigned exam report signing". As described above, the task information processing unit 104 may generate information on new tasks in accordance with the result of performing the tasks necessarily generated for the order. The writing control unit 120 writes the generated task information in the task information storing unit 140.

Figure 11:
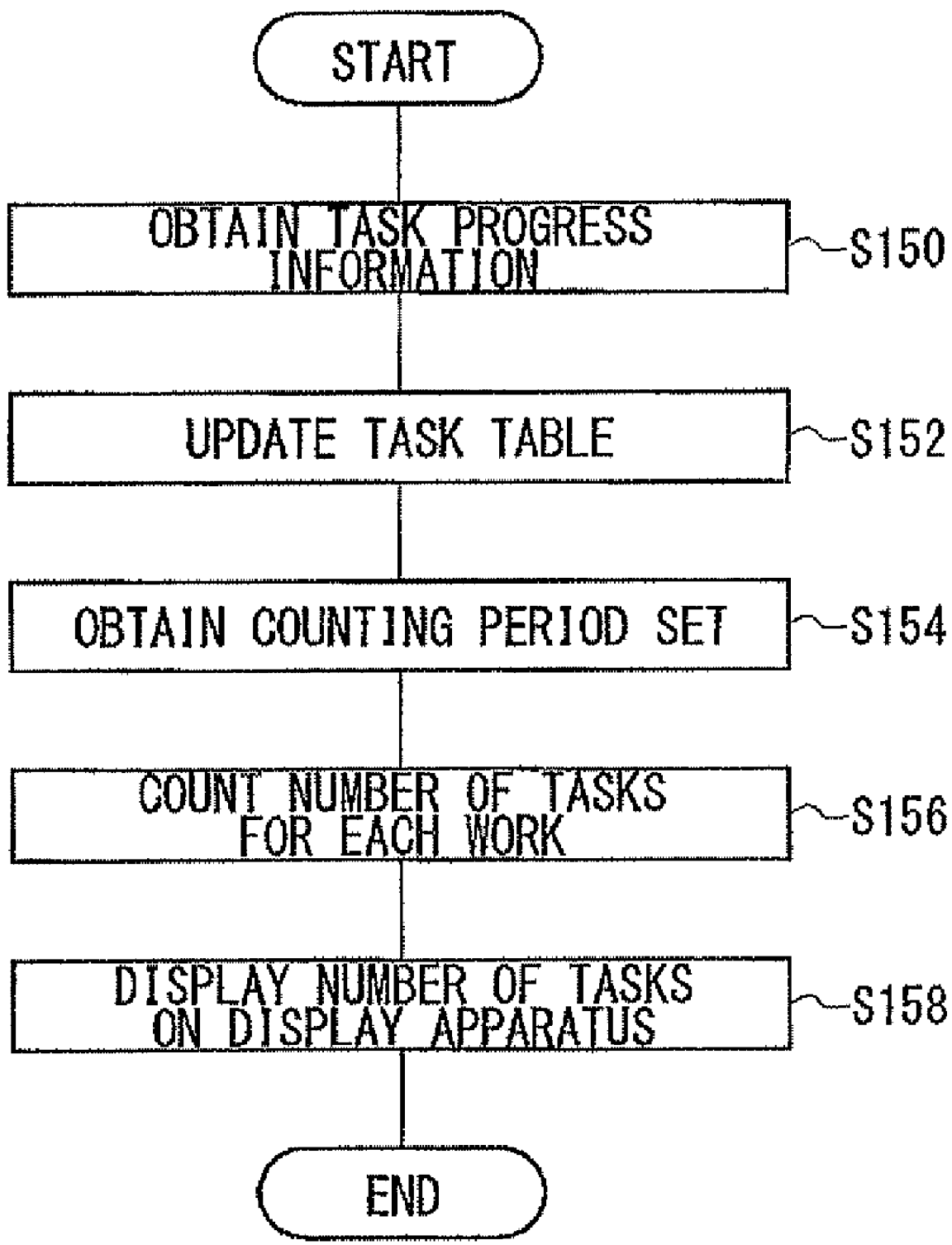
FIG. 11 is a view showing a display updating flow when a task is completed during the display of the number of tasks to be executed.

FIG. 11 shows the display updating flow when a task is completed during the display of the number of the tasks to be executed. When the task information processing unit 104 receives the task progress information (S150), the writing control unit 120 writes the task progress information in the task information storing unit 140. The search processing unit 124 updates the task table, taking the task progress information into account (S152). The task number counting unit 126 obtains the set counting period from the counting period memory unit 130 (S154) and counts the number of the tasks to be executed in accordance with the set counting period (S156). The display control unit 128 embeds the number of the tasks to be executed in the screen template and displays the screen template on the display apparatus (S158).

Not only the aforementioned embodiment but the combinations of the elements of the embodiments will also be within the scope of the present invention. Various variations including design variations can be made to the embodiments by those skilled in the art and such variations are also within the scope of the present invention. Some such examples are shown in the following. For example, the numbers of the tasks to be executed are displayed with icons as shown in FIG. 8; however, the numbers of the tasks to be executed may be displayed adjacent to the text showing the details of the service.

In the embodiment, only the numbers of the tasks to be executed are displayed; however, the numbers of the tasks already executed can be displayed at the same time. By having the numbers of the tasks to be executed and the numbers of the tasks already executed displayed at the same time, the person in charge can check the outcome of the job of the day and the future schedule. Thus, the person in charge can keep track of the progress information on the day intuitively.

By having the number of the tasks to be executed displayed, a nurse can, for example, judge whether there is enough drugs in the examination room. As described above, the medical information management apparatus 10 enables the confirmation of the number of the tasks to be executed. With this, the medical information management apparatus 10 can offer enhanced usability such that not only the user can keep track of the service status but also the progress of service is facilitated.

The medical information management system 1 can provide the user with the further useful functions. For example, the medical information management apparatus 10 may provide the user with a time capture function. This time capture function enables the behavior of the patient and the time at which the medical treatment is administered on the patient to be easily captured so that the event recording of the patient can be easily made.

Figure 12:
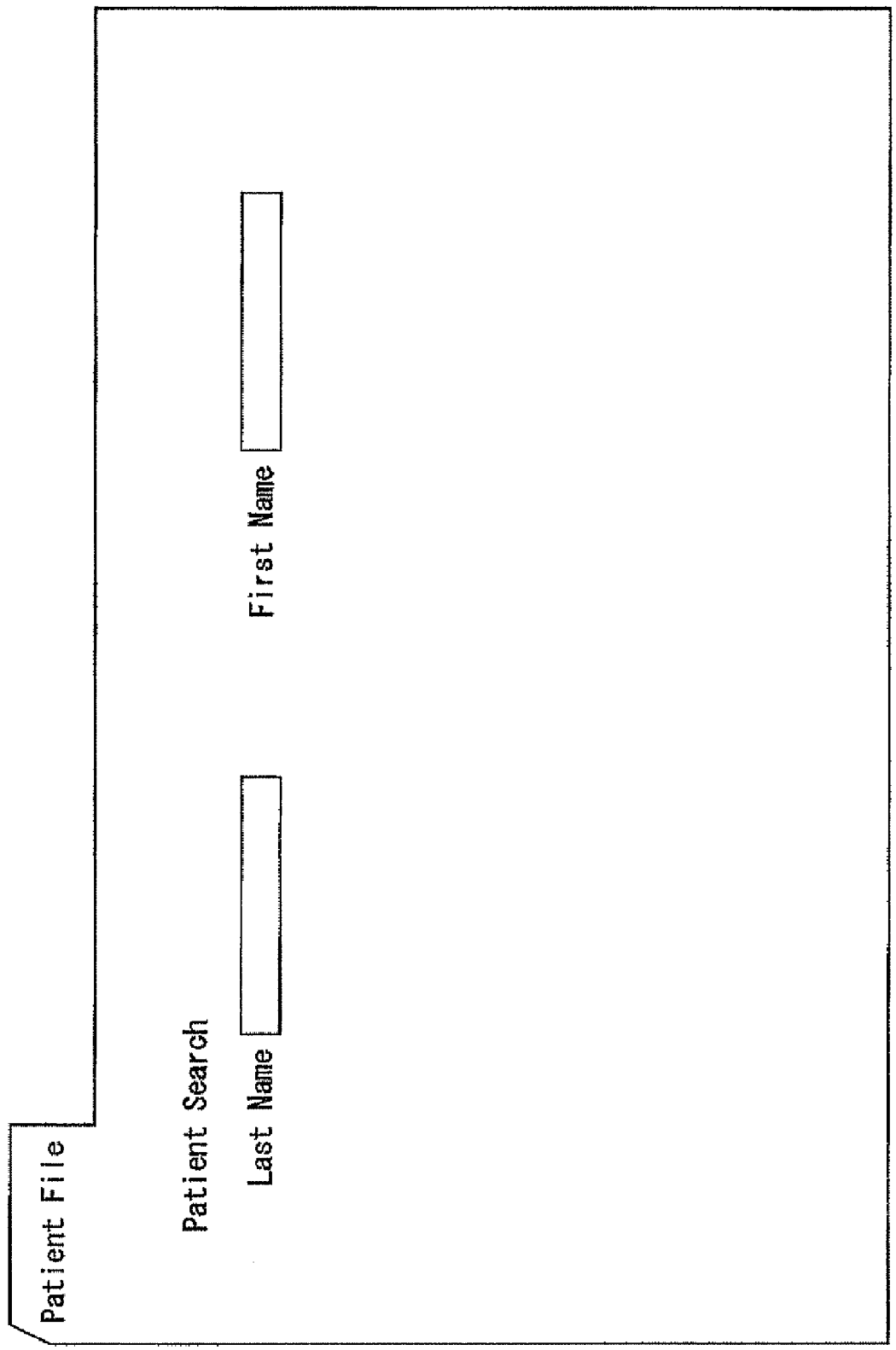
FIG. 12 is a view showing an input screen to input a patient name.

FIG. 12 shows the input screen to input a patient name. Inputting the name of the patient permits a patient event report to be created and displayed. The patient event report may be displayed by inputting not the name of the patient but the information to specify the patient, for example, a patient code.

Figure 13:
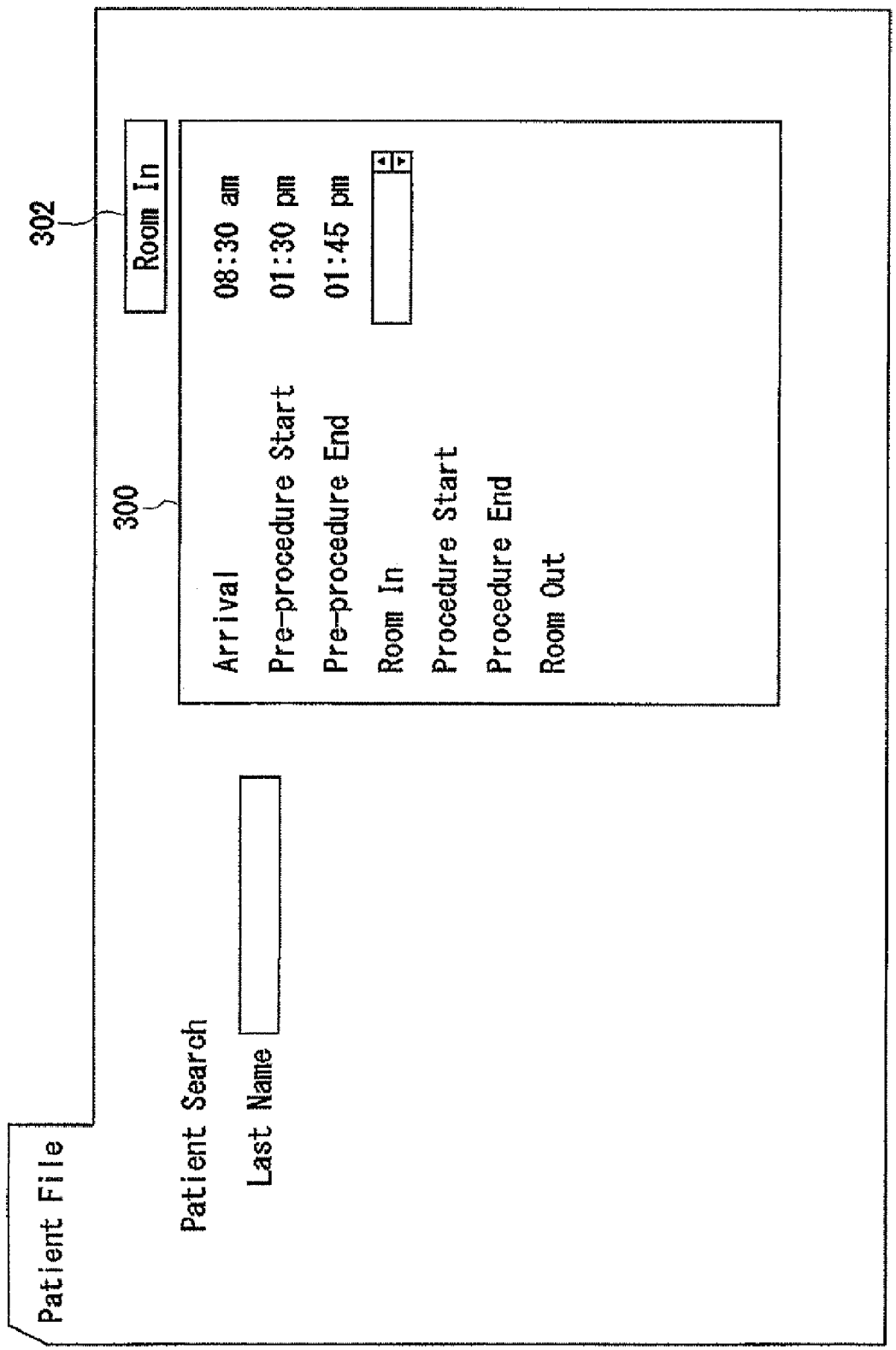
FIG. 13 is a view showing a patient event report.

FIG. 13 shows a patient event report 300. The event report is created by, for example, a nurse. The nurse can write the time of that moment in the event report 300 by pushing down a time capture button 302, using an input apparatus. The name of the schedule which is up next is displayed on the time capture button 302; and in the case of FIG. 13, it is shown that the patient is waiting to enter the examination room. When the nurse confirms the entry of the patient to the examination room, he or she pushes the time capture button 302, and the medical information management apparatus 10 records in the event report 300 the time at which the button is pushed. When the time is recorded, it is shown that the patient is waiting for the "examination start" and the nurse in the examination room pushes the time capture button when the examination starts. As described above, the event recording of the patient can be easily created by adding the time capture function to the medical information management apparatus 10.

Figure 17:
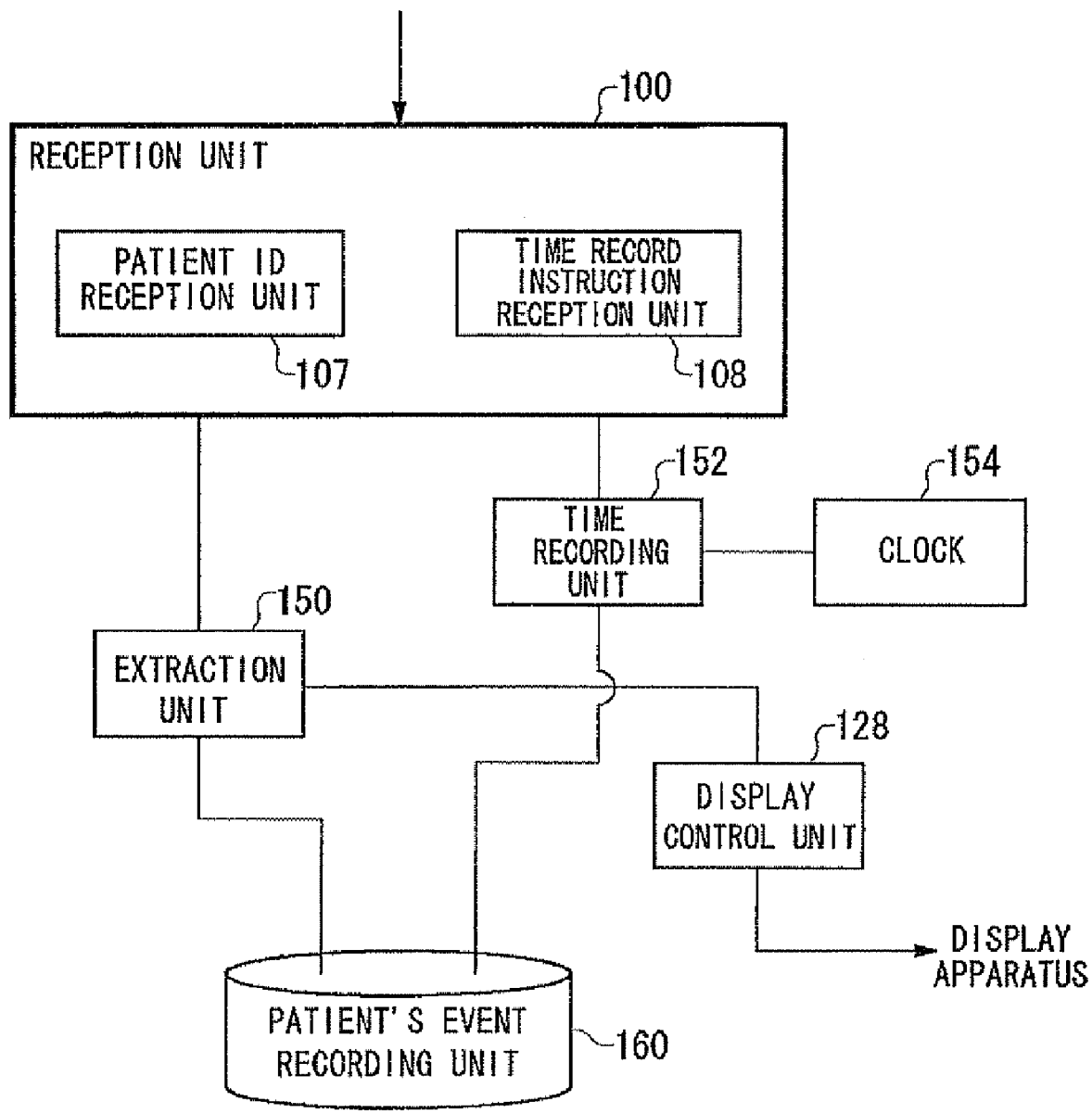
FIG. 17 is a view showing an example of variation of a medical information management apparatus.

FIG. 17 shows an example of variation of a medical information management apparatus. The medical information management apparatus 10 is provided with a reception unit 100, an extraction unit 150, a time recording unit 152, a clock 154, a display control unit 128, and a patient's event recording unit 160. The reception unit 100 has a patient ID reception unit 107 and a time record instruction reception unit 108. The patient's event recording unit 160 keeps schedule data recording a name of the schedule showing the event of the patient's behavior in a medical institution or a name of the schedule showing "start" or "end" for the task to be performed on the patient in association with the execution time.

When the patient ID reception unit 107 receives the identification information specifying the patient, the extraction unit 150 extracts the schedule data of the patient whose identification information is received by the patient ID reception unit 107 from the patient's event recording unit 160. The schedule data includes multiple series of names of the schedule showing events of the patient's behavior in the medical institution and "start" or "end" for the tasks to be performed on the patient and is forwarded to the display control unit 128. In the schedule data, the execution time is associated with the names of the schedule for the tasks already executed.

In a display apparatus, in addition to displaying multiple names of the schedule included in the schedule data in the order of execution, the display control unit 128 displays the execution time for the names of the schedule for the tasks already executed, associating them with each other. The display control unit 128 further displays the time capture button 302 for displaying the name of the schedule for the task to be performed subsequently. With this, the patient event report is generated. When the time capture button 302 is pushed, the time record instruction reception unit 108 receives the pushing manipulation and notifies the time recording unit 152 of the pushing manipulation. The time recording unit 152 receives the time of the pushing manipulation from the clock 154 and records the time in the patient's event recording unit 160, associating the time with the name of the schedule displayed on the time capture button 302. With this, when the time capture button 302 is pushed, the patient's event recording unit 160 can record the name of the schedule and the time at which the button is pushed, associating them with each other. Therefore, the patient event report 300 can be generated with simple manipulation.

Also, the medical information management apparatus 10 may provide the user with a report writing support function. The report writing support function enables the user to select words so as to create a report semi-automatically.

FIG. 14 shows a word selection screen displayed on a display apparatus. Prepared words are listed in the left column of the display screen. Upon the selection of any one of the words in the left column, a word selection screen 400 in regard to the selected word is displayed. In FIG. 14, the word "polyps" is selected and the word selection screen 400 offering word options to be input in relation to polyps (e.g., "number" and "size") is displayed. In FIG. 14, a screen is shown having a plurality of words selected by the user. At least a part of word choices is structured hierarchically, and upon the selection of such words, the word choices prepared in the lower level are displayed. By selecting these words accordingly, the sentences required for the report are created semi-automatically.

FIG. 15 shows a written report. In a report 402, the underlined parts are the words selected from a word group by the user. The medical information management apparatus 10 prepares the sentence model to write the report 402, and by letting the user to select the words to fill in the blanks in the sentence model, the report 402 becomes completed. Provided with this kind of report writing support function, the medical information management apparatus 10 can provide useful working environment to the user.

As described previously, the word group is structured hierarchically. Thus, when the user wish to select a word in the lower level, the user must access the word in accordance with the hierarchical structure. In case of the word which is often used, it is possible for the user to memorize how to access the word; however, it is not easy in case of the word which is barely used. The medical information management apparatus 10 has a function of providing the user with an access route to the desired word.

FIG. 16 shows the access route to the desired words. The user inputs in a search field 406 the word he or she wishes to include in the report. In the figurer a word "H. Plylori antibody test" is input. The medical information management apparatus 10 searches for the route to access the word and displays the searched route options on a route presenting screen 404. In FIG. 16, the route options are presented of the routes from three words provided in the left column, "cytology", "polyps", and "tumor" to the word "H. Pylori antibody test".

For example, if the route presented in the middle of the route presenting screen 404 which begins from the word "polyps" is selected, the word "cytology" under the word "maneuvers" in the word selection screen 400 is selected and the word "H. Pylori antibody test" which is in the further lower level is also selected. As described above, presenting to the user the route to the word which he or she wishes to input permits the user to easily select the desired word With this, the time required for the completion of the word selection can be shortened; and thus, the report can be written in a short time.

What is claimed is:

1. A medical information management apparatus which manages information on a medical service, comprising:

an identification information reception unit operative to obtain identification information that identifies a person or group in charge;

a storing unit operative to store progress information indicating whether tasks generated in a plurality of medical services are executed or not yet executed, each of said tasks associated with one medical service and each task and each medical service stored in association with the identification information of the person or group in charge;

a search processing unit operative to search for a task generated for a medical service associated with the identification information obtained at the identification information reception unit;

a task number counting unit operative to count a number of tasks not yet executed and searched for by the search processing unit, for each medical service;

a display control unit operative to display on one screen of a display apparatus a plurality of the counted numbers of tasks, each of the numbers displayed in association with an icon showing detail of one of the plurality of medical services;

a counting period memory unit operative to store the period for the counting by the task number counting unit, wherein the storing unit stores a task generated for a predetermined medical service in association with a scheduled execution date thereof, and the task number counting unit counts the task not yet executed whose scheduled execution date falls in the period stored in the counting period memory unit;

a patient's event recording unit that records a name of a schedule showing an event of a patient's behavior in a medical institution or a name of a schedule showing "start" or "end" for a task to be performed on the patient in association with execution time;

a patient identification information reception unit operative to receive identification information that specifies a patient; and an extraction unit operative to extract schedule data of the patient whose identification information is received by the patient identification information reception unit from the patient's event recording unit, wherein in addition to displaying a plurality of names of the schedule included in the schedule data in the order of execution, in the display apparatus, the display control unit displays the execution time for the names of the schedule for the tasks already executed in association with the names of the schedule, and further displays a button for displaying a name of the schedule for a task to be performed subsequently, and the patient's event recording unit records the time at which the button is pushed in association with the name of the schedule which is displayed in the button when the button is pushed.

2. The medical information management apparatus according to claim 1, further comprising:

a designated period reception unit operative to receive the information on the designated period, wherein the storing unit stores a task generated for a predetermined medical service in association with a scheduled execution date thereof, and the task number counting unit counts the task not yet executed whose scheduled execution date falls in the period received at the designated period reception unit.

3. The medical information management apparatus according to claim 1, further comprising:

a screen template memory unit operative to store a screen template for respective person or group in charge, wherein the display control unit selects a screen template based on the identification information.

4. The medical information management apparatus according to claim 1, further comprising:

a task information processing unit operative to generate information on first tasks generated for an issued order and information on second tasks generated in accordance with results of the first tasks, wherein the task number counting unit counts the number of tasks not yet executed from the first tasks and the second tasks, and the display control unit displays the counted number of tasks on the display apparatus.

5. The medical information management apparatus according to claim 4, wherein the task information processing unit generates the information on the second task in accordance with the result of performing the first task.

6. The medical information management apparatus according to claim 1, wherein the number of tasks not yet executed indicates an amount of remaining services.

7. The medical information management apparatus according to claim 1, wherein the person or group in charge is one or more of doctors, nurses, receptionists, and members of the staff in the medical professions division.

8. The medical information management apparatus according to claim 1, wherein the plurality of medical services are generated in an endoscopic examination.

9. The medical information management apparatus according to claim 8, wherein the tasks comprise activities to be executed during the performance of the endoscopic examination.

* * * * *